United States Patent [19]

Seiden et al.

[11] Patent Number: 4,607,342
[45] Date of Patent: Aug. 19, 1986

[54] APPARATUS FOR REMOTELY MEASURING AND CONTROLLING THE CARBON DIOXIDE IN A BEVERAGE LIQUID: ON-LINE

[75] Inventors: Louis W. Seiden, Rockville; Dennis R. Stone, Burtonsville; Kenneth G. Neimiller, Odenton, all of Md.

[73] Assignee: Water Quality Sciences, Inc., Rockville, Md.

[21] Appl. No.: 463,526

[22] Filed: Mar. 4, 1983

[51] Int. Cl.[4] .................. G01N 7/00; G01N 33/497
[52] U.S. Cl. .................................. 364/558; 73/19; 340/611; 364/500
[58] Field of Search ............ 364/500, 501, 502, 558, 364/200; 73/19; 340/611, 825.06

[56] References Cited

U.S. PATENT DOCUMENTS

| | | |
|---|---|---|
| 3,077,765 | 2/1963 | Dijkema .................................. 73/19 |
| 3,800,288 | 3/1974 | Russell et al. ...................... 364/200 |
| 4,179,918 | 12/1979 | Van Strien ............................. 73/19 |
| 4,396,977 | 8/1983 | Slater et al. ...................... 364/500 X |
| 4,420,811 | 12/1983 | Tarnay et al. .................. 364/502 X |
| 4,424,559 | 1/1984 | Lorincz et al. ................. 364/500 X |

Primary Examiner—Felix D. Gruber
Assistant Examiner—Kevin J. Teska

[57] ABSTRACT

This device periodically isolates a sample of a beverage in production and determines the level of Carbon Dioxide present in the sample by the pressure temperature method. This system eliminates the overpressure in the line and then computes the carbonation level in the beverage to the same precision as standard laboratory instruments. The line pressure is often higher than the equilibrium pressure in the finished container by a significant factor (1.5 to 2) and is also fluctuating. By properly equilibriating the sample before testing these problems are eliminated.

1 Claim, 1 Drawing Figure

APPARATUS FOR REMOTELY MEASURING AND CONTROLLING THE CARBON DIOXIDE IN A BEVERAGE LIQUID: ON-LINE

BACKGROUND OF THE INVENTION

1. Technical Field

Since the measurement has two fundamental independent variables—pressure and temperature—both variables must be read accurately and at the proper moment in order to get reliable data. Assume temperature presents no difficultly. Pressure measurements are a problem for two reasons.

A. The zero pressure point is not known due to electronic offset, electronic drift, or atmospheric changes. In an on-line operation one must only know the range of the pressure transducer (normally 100 pounds calibrated by dead weight tester). For example, the constant or fixed offset may be +5 lbs. If the chamber is open to atmospheric pressure the computer will read and remember an offset of (+5+delta) pounds. Delta is an additional change due to variations in atmospheric pressure or electronic drift. (These two parameters are not easily separated.) Extensive work has shown that the range calibration is independent of any offset. Therefore proper zeroing (in the example zero is defined as 5+delta pounds) is necessary to get the proper pressure. The final or measurement pressure is (P−(C+delta)) where C is the constant part of the offset and delta is the variable part of the offset.

B. There is an overpressure in the flow line due to the fact that $CO_2$ is supplied to the liquid at a pressure beyond that which can be dissolved in the beverage. By venting to the atmosphere for the same time for each type of beverage, using the third valve (equilibrium valve or timing valve), one can precisely determine the ideal time to take a measurement such that the overpressure is bled off but none of the dissolved gas has left the liquid.

TABLE 1

A typical example - the comparison between a lower pressure beverage and a higher pressure beverage.

|  | LOWER PRESSURE BEVERAGE | HIGHER PRESSURE BEVERAGE |
|---|---|---|
| Line pressure | 30 lbs. | 45 lbs. |
| Pressure of $CO_2$ from drink after bleed and agitation | 18.8 lbs. at 36.5 F. | 24 lbs. at 36.5 F. |
| Final $CO_2$ | 3.34 volumes | 4.05 volumes |
| Bleed time (measurement at equilibrium solenoid valve) | .150 seconds | .850 seconds |

Table shows the transition from a beverage oversaturated with $CO_2$ in the line to a beverage with the proper amount of $CO_2$ suitable for an on-line measurement. The calibrated leak (determined by the structure of the equilibrium solenoid valve) to the atmosphere must be timed (bleed time) to get precise and repeatable $CO_2$ volumes that compare favorable with the laboratory backup test. The laboratory test is generally a pressure, temperature measurement similar to the on-line measurement. Different drinks required different bleed times. Some control as provided by a small computer is necessary to implement this measurement. (Note: the word sniff may be used interchangeably with the word bleed for historical reasons.)

A well-defined and repeatable bleed time is an important variable in accurately determining the pressure due only to the dissolved gas in the liquid. The sample is then agitated in the closed chamber and the resulting pressure is defined as the $CO_2$ pressure of the drink. (Note: the computer has subtracted the zero pressure which it has in memory.)

2. Background Art

The Pressure and Temperature method is a traditional technique for deriving $CO_2$ volumes. Most, if not all, pressure, temperature, and volume measurements are based on Heath's table (See Table 2).

The Effect of Temperature and Pressure Changes Expressed in Pounds per Square Inch and in Degrees Fahrenheit. A very useful solubility table has been calculated by Heath* in which the data are expressed in English engineering units. These data are specially useful to the bottling industry and they are here reproduced as Table 2.

TABLE 2

The Solubility of Carbon Dioxide in Water at Various Temperatures in °F. and Various Pressures in lbs. per sq. in. Gage. Table shows the volume of carbon dioxide measured at 32° F. and 14.7 lbs./sq. in. which dissolves in one volume of water at the temperature and pressure indicated. (Calculated by Heath)

| P lbs./ sq. in. | Temperature °F. | | | | | | | | | | | | |
|---|---|---|---|---|---|---|---|---|---|---|---|---|---|
|  | 32 | 36 | 40 | 44 | 48 | 55 | 60 | 65 | 70 | 75 | 80 | 85 | 90 |
| 15 | 3.46 | 3.19 | 2.93 | 2.70 | 2.50 | 2.20 | 2.02 | 1.86 | 1.71 | 1.58 | 1.84 | 1.35 | 1.27 |
| 20 | 4.04 | 3.73 | 3.42 | 3.15 | 2.92 | 2.57 | 2.36 | 2.17 | 2.00 | 1.84 | 1.69 | 1.58 | 1.48 |
| 25 | 4.58 | 4.27 | 3.92 | 3.61 | 3.35 | 2.04 | 2.69 | 2.48 | 2.29 | 2.10 | 1.93 | 1.80 | 1.70 |
| 30 | 5.21 | 4.81 | 4.41 | 4.06 | 3.77 | 3.31 | 3.03 | 2.80 | 2.58 | 2.37 | 2.18 | 2.03 | 1.91 |
| 35 | 5.80 | 5.35 | 4.91 | 4.52 | 4.19 | 3.69 | 3.37 | 3.11 | 2.86 | 2.63 | 2.42 | 2.26 | 2.13 |
| 40 | 6.37 | 5.89 | 5.39 | 4.97 | 4.61 | 4.05 | 3.71 | 3.42 | 3.15 | 2.89 | 2.67 | 2.49 | 2.34 |
| 45 | 6.95 | 6.43 | 5.88 | 5.43 | 5.03 | 4.43 | 4.06 | 3.74 | 3.44 | 3.16 | 2.91 | 2.72 | 2.56 |
| 50 | 7.53 | 6.95 | 6.36 | 5.89 | 5.45 | 4.80 | 4.40 | 4.05 | 3.73 | 3.42 | 3.16 | 2.94 | 2.77 |
| 55 | 8.11 | 7.48 | 6.86 | 6.34 | 5.87 | 5.17 | 4.74 | 4.37 | 4.02 | 3.69 | 3.40 | 3.17 | 2.99 |
| 60 | 8.71 | 8.02 | 7.35 | 6.79 | 6.29 | 5.53 | 5.08 | 4.68 | 4.31 | 3.95 | 3.64 | 3.39 | 3.20 |
| 70 | 9.86 | 9.09 | 8.33 | 7.70 | 7.13 | 6.27 | 5.76 | 5.30 | 4.89 | 4.49 | 4.14 | 3.86 | 3.63 |
| 80 | 11.02 | 10.17 | 9.31 | 8.61 | 7.98 | 7.00 | 6.43 | 5.92 | 5.46 | 5.02 | 4.62 | 4.31 | 4.06 |
| 90 | 12.18 | 11.25 | 10.30 | 9.52 | 8.82 | 7.74 | 7.11 | 6.54 | 6.04 | 5.55 | 5.12 | 4.77 | 4.49 |

TABLE 2-continued

The Solubility of Carbon Dioxide in Water at Various Temperatures in °F. and Various Pressures in lbs. per sq. in. Gage. Table shows the volume of carbon dioxide measured at 32° F. and 14.7 lbs./sq. in. which dissolves in one volume of water at the temperature and pressure indicated.
(Calculated by Heath)

| P lbs./ | Temperature °F. | | | | | | | | | | | | |
|---|---|---|---|---|---|---|---|---|---|---|---|---|---|
| sq. in. | 32 | 36 | 40 | 44 | 48 | 55 | 60 | 65 | 70 | 75 | 80 | 85 | 90 |
| 100 | 13.34 | 12.33 | 11.29 | 10.43 | 9.66 | 8.40 | 7.79 | 7.18 | 6.62 | 6.08 | 5.60 | 5.22 | 4.91 |

SUMMARY OF THE INVENTION

The pressure temperature technique for determining the carbonation ($CO_2$) content can be traced back to the works of Wroblewski (1), Bohr (2), and Heath (3). Heath first printed his well-known table concerning the solubility of Carbon Dioxide in water at various temperatures in degrees Fahrenheit in Atlanta, GA in 1915. This invention is based upon this earlier work and allows the pressure, temperature technique to be automated for on-line measurement and control of the $CO_2$ content in a beverage liquid. This device overcomes the problems of separating true or gage pressure from absolute pressure, electronic offset, and electronic drift. It also overcomes the problem of overpressured sample lines by creating a balanced condition before the agitation pressure measurement occurs. Previous efforts to measure on-line $CO_2$ are described by Dijkema (U.S. Pat. No. 3,077,765) and van Strien (U.S. Pat. No. 4,179,918).

[1] Wroblewski, S., Compt. rend., 94, 1335 (1882).
[2] Bohr, C., Ann. Physik., 68, 500 (1889).
[3] Heath, W. P., Privately Printed, Atlanta, Ga., (1915).

DESCRIPTION OF THE PREFERRED EMBODIMENT

Figure 1:
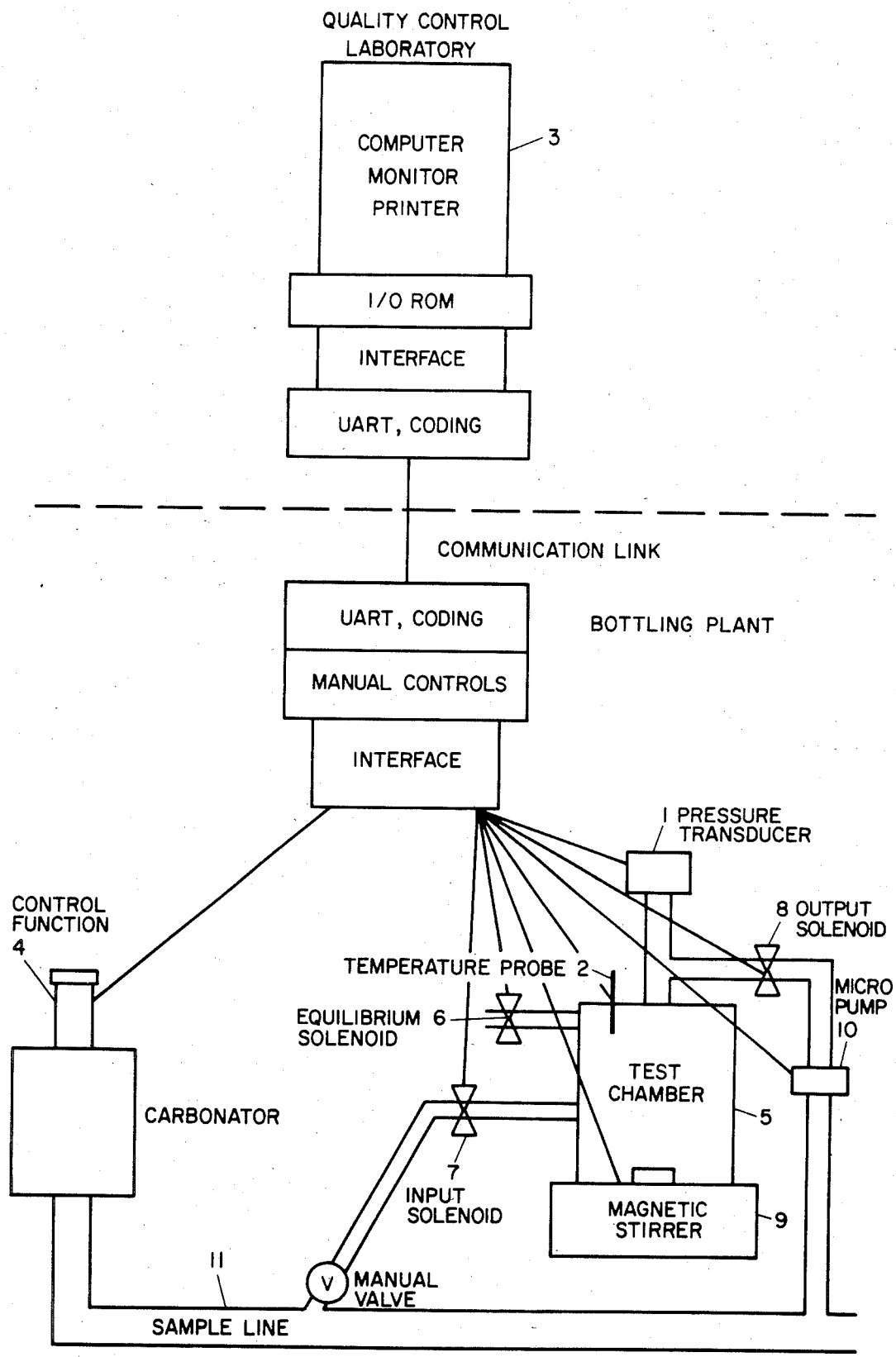
FIG. 1 is a general block diagram of the system for measurement and control of $CO_2$ in a beverage liquid flow line.

An apparatus to remotely control and periodically measure the $CO_2$ in a beverage line is shown in FIG. 1. This apparatus isolates a sample from the line, brings the sample to equilibrium, agitates the sample, takes pressure (1) and temperature (2) measurements, and calculates the $CO_2$ by an on-line computer (3) or microprocessor as a function of pressure and temperature. The sample is tested periodically and the system is software controlled. At the beginning of the cycle an operator enters certain data such as high and low limits for the volumes of $CO_2$ present in the liquid, agitation time, and time between samples. The high-low limits allow the sample $CO_2$ reading to be checked and if out of limits an alarm is actuated and remedial action taken which in extreme circumstances allows the system to be automatically shut down and in normal circumstances allows the system to be controlled. A control signal is delivered to a stepping motor (4) or a similar device which allows the pressure of the $CO_2$ to be adjusted at the source. In sequence, the system under computer control first checks and then corrects the zero offset which may be due to electronic offset, electronic drift, or atmospheric changes. This is accomplished by opening a sample chamber (5) via an equlibrium valve (6) to atmospheric pressure. The resulting pressure measurement is saved and later subtracted from sample data. The input (7) and output valves (8) are again opened and the equilibrium valve closed. All three valves are then closed when a measurement is signaled for. At this point the system is checked for overpressure—the $CO_2$ pressure in the line which is considerably higher than the equilibrium pressure in the liquid and does not relate to the $CO_2$ in the beverage. The overpressure is then automatically bled off at the equilibrium valve and a magnetic stirrer (9) turned on for agitation (also propeller and ultrasonic devices are applicable for agitation). After the sample is agitated for a fixed time, the stirrer is then remotely turned off. Data (pressure and temperature) is then taken several times to insure first that there are no communications errors and second that there are no leaks in the test apparatus. The proper $CO_2$ formula or table is then used to computer $CO_2$ volumes. Most, if not all, formulas and tables are derived from Heath's work. (See Background—Table 2) Finally, the date, sample time, high-low limits, pressure, temperature, and volume of $CO_2$ are displayed on a printer at the remote site. If the data is outside the limits, warnings are observed and corrective action is taken. A small pump (10) may be used to enhance the flow of the sample through the test chamber and back into the sample line (11).

We claim:

1. A system for remotely measuring and controlling the $CO_2$ content of a beverage line liquid in a periodic fashion such that there are three computer controlled solenoid valves—the first valve for sample input, the second valve for sample output, and the third valve (equilibrium valve or timing valve) for automatically zeroing a pressure transducer and relieving an overpressure in the line; wherein the third solenoid valve automatically zeros the pressure transducer for offset, atmospheric changes, and drift prior to $CO_2$ measurement; and during said measurement, automatically bleeds the overpressure in the line for a predetermined period of time based upon the type of beverage being measured.

* * * * *